United States Patent [19]

Bailey et al.

[11] Patent Number: 5,314,822
[45] Date of Patent: May 24, 1994

[54] METHOD OF CLONAL GROWTH OF STREPTOCOCCUS PNEUMONIAE

[75] Inventors: Fred J. Bailey, Hatfield; Wayne K. Herber, Center Valley, both of Pa.

[73] Assignee: Merck & Co., Inc., Rahway, N.J.

[21] Appl. No.: 961,587

[22] Filed: Oct. 15, 1992

[51] Int. Cl.$^5$ ............................................. C12N 1/20
[52] U.S. Cl. ........................... 435/253.4; 435/253.1; 435/253.6; 435/252.1
[58] Field of Search ............... 435/253.1, 253.4, 253.6, 435/252.1

[56] References Cited

U.S. PATENT DOCUMENTS

| | | | |
|---|---|---|---|
| 4,355,111 | 10/1982 | Shimizu et al. | 435/252.1 |
| 4,686,102 | 8/1987 | Ritchey et al. | 424/92 |
| 4,695,624 | 9/1987 | Marburg | 530/395 |

OTHER PUBLICATIONS

Rane, et al., *J. Bacterial*, 40:695–704 (1940).
Adams, et al., *J. Bacterial*, 49:401 (1945).
Bohons & Sabborow, *Arch. Biochem.*, 3:257–259 (1943).
Holdeman et al. eds, *Anaerobe Lab. Manual*, 4th edn, (1977).
Brooks et al, *J. of Clinical Microbio.*, 11:45–51 (1980).
Bernheimer et al, *J. Bacteriol.*, 43:495–498 (1942).
Holt, *J. Gen Microbiol.* 27:327–330 (1962).
Markowitz, A. S. and Henderson, J. R. Nature, 181:771–772 (1958).
Bernheimer and Pappenheimer, Jr., *J. Bacterial.*, 43:481–494 (1942).
Hoeprich, *J. Bacterial.*, 74:587–590 (1957).
Hoeprich, *J. Bacterial.*, 69:682–688 (1955).
Wright, *J. Path. and Bacterial.*, 37:257–282 (1933).
ATCC Catalogue of Bacteria and Phages 17th ed 1989 pp. 339, 334.
Cano and Colome *Essentials of Microbiology* 1988 pp. 88–89.

*Primary Examiner*—David M. Naff
*Assistant Examiner*—Deborah K. Ware
*Attorney, Agent, or Firm*—Gerard H. Bencen; Jack L. Tribble; Paul D. Matukaitis

[57] ABSTRACT

A culture medium containing no complex animal components is useful for production of bacteria and inoculum development from which pharmaceutically important products are to be isolated.

2 Claims, No Drawings

METHOD OF CLONAL GROWTH OF *STREPTOCOCCUS PNEUMONIAE*

BACKGROUND OF THE INVENTION

Production of compounds of pharmaceutical significance by culturing bacteria and isolation of products produced in culture is an expanding field of science. An impediment to obtaining regulatory approval for products produced in this manner is encountered whenever the bacterial organism being cultured requires complex animal components for its growth. For example, culture of *Streptococcus pneumoniae* (pneumococci), to produce pneumococal polysaccharides for vaccine production, particularly at the inoculum development stage, is typically performed in media containing complex bovine or ovine derived products such as peptones, gelatins, caseins, or blood derived products. *S. pneumoniae* are known to be fastidious, having nutritional requirements for choline [Rave et al., *J. Bact.*, 40, 695–704 (1940)], vitamins [Adams et al., *J. Bact.*, 49 401–409 (1945)], and biotin. [Bohonos and Sabborow, *Arch. Biochem.* 3, 257–259 (1943)]. Even where subsequent culture of bacteria in media free of complex bovine or ovine derived products has been achieved, initial development of the culture inoculum of *S. pneumoniae* has been accomplished in blood-containing or bovine/ovine derived product media. This invention demonstrates the feasability of inoculum development in a medium devoid of these complex and potentially troublesome components.

One commercially available medium useful for bacterial culture is known as PYG. PYG contains:

| | |
|---|---|
| peptone | 5 g |
| trypticase | 5 g |
| yeast extract | 10 g |
| resazurin solution | 4 ml |
| salts solution | 40 ml |
| distilled water | 1000 ml |
| hemin solution | 10 ml |
| vitamin K | 0.2 ml |
| cysteine HCl.H$_2$O | 0.5 g |
| glucose | 10 g |

(see *Anaerobe Laboratory Manual*, 4th Edition, 1977, Holdeman et al. eds; Virginia Polytechnic Institute and State University, Blacksburg, Va. 24061, p13). *S. pneumoniae* can be cultured in this medium, but since the medium contains beef peptone, it is not desirable for production of vaccine components.

One significant reason for using a culture medium free of animal or blood products is to reduce or avoid the possibility of contamination by agents which cause spongiform encephalopathies, such as Prion Disease [see, for example, *The Lancet*, vol. 336, p21–22, Jul. 7, 1990, and references cited therein]. The etiologic agent of such diseases as scrapie in animals, Creutzfeldt-Jakob disease, Gerstmann-Straussler syndrome, and kuru in man, is thought to be transimissible by animal blood products, particularly bovine or ovine derived products.

We have discovered a culture medium completely devoid of complex animal derivatives which nonetheless supports the growth of the pneumococci, such as *Streptococcus pneumoniae* strains (Danish nomenclature based on serotype) 1, 2, 3, 4, 5, 6B, 7F, 8, 9V, 9N, 10A, 11A, 12F, 14, 15B, 17F, 18C, 19F, 19A, 20, 22F, 23F and 33F. The medium does not contain bovine or ovine-derived products, nor does it contain blood. Furthermore, the inocula derived in this new medium can be used to initiate production of the pneumococcal capsular polysaccharide which can be harvested and used to prepare vaccines, as described for example in U.S. Pat. No. 4,695,624.

The advantage of this new medium is the elimination of animal components (especially bovine or ovine derived products) from the product production process. By eliminating animal components, the dangers of contamination with reactive blood group substances or adventitious agents are reduced, and the need to remove these contaminants during purification is eliminated. It also becomes less necessary to demonstrate the absence of such contaminants in the final vaccine product.

Thus, according to this invention, a new medium composition for culturing bacteria is provided. A method for using said composition, particularly for inoculum development, is also provided. The invention will allow production of fastidious bacteria such as *S. pneumoniae*, and frozen seed stocks thereof which have not had contact with bovine or ovine derived materials. This will facilitate the regulatory review process for the pharmaceutical products derived from culture of such organisms. Thus, according to this invention, culture growth and inoculum development can be obtained in a medium free of bovine or ovine derived products. Furthermore, the invention provides an alternate and preferred culture medium and method for production of inocula for pneumococcal capsular polysaccharide production.

SUMMARY OF THE INVENTION

A culture medium is provided which contains no bovine, ovine, or crude blood derived products, but which is effective to support inoculum development for growth of *Streptococcus pneumoniae* and production of pneumococcal capsular polysaccharide for vaccine production. In a preferred formulation of the medium, the medium comprises: modified peptone yeast base, salt solution, resazurin, vitamin K, hemin, sodium bicarbonate, L-cysteine HCl, glucose, and HEPES buffer.

DETAILED DESCRIPTION OF THE INVENTION

One preferred formulation of the medium of this invention contains the following ingredients per liter:

| | |
|---|---|
| Yeast Extract | 10 g |
| Soy Peptone | 10 g |
| Salt Solution | 20 ml |
| Resazurin | 1 mg |
| Vitamin K | 0.5 mg |
| Hemin | 5 mg |
| Sodium Bicarbonate | 0.4 g |
| L-cysteine HCl | 0.85 g |
| Glucose | 10 g |
| HEPES buffer (pH 7.3–7.8) | 47.66 g |

This specific formulation has been named SYG medium. However, it should be understood that the very precise amounts of ingredients provided above may be optimized, or modified so long as no animal products are introduced. The key aspect of the medium is the absence of blood, bovine or ovine derived products and the ability of the medium to support growth of *Streptococcus pneumoniae* and thereby the production of pneumococcal polysaccharides useful for vaccine production.

The modified Soy peptone and yeast base are hydrolysates of yeast and soy proteins. Several commercial sources for these components are available. We have found that Difco yeast extract and Sheffield HY-SOY PEPTONE are quite acceptable for this purpose.

The salt solution may contain:

| | |
|---|---|
| $CaCl_2$ (anhydrous) | 0.2 g |
| $MgSO_4$ (anhydrous)* | 0.2 g |
| $K_2HPO_4$ | 1.0 g |
| $KH_2PO_4$ | 1.0 g |
| $NaHCO_3$ | 10.0 g |
| NaCl | 2.0 g |

(Mix $CaCl_2$ and $MgSO_4$ in 300 ml distilled water until dissolved. Add 500 ml water and, while swirling, slowly add remaining salts. Continue swirling until all these salts are dissolved. Add 200 ml distilled water, mix and store at 4 C. * Alternatively, use 0.48 g $MgSO_4.7H_2O$). Other compositions for the salt solution may also be acceptable, so long as sufficient buffering and osmolarity are maintained.

The resazurin is completely optional and it may be eliminated or replaced with another indicator as desired. Its sole purpose is to indicate the redox potential of the medium. If included, it may be prepared as follows: Dissolve 25 mg resazurin in 100 ml distilled water. Resazurin is available in powder form from Fisher, Difco and Baker.

Vitamin K may be required, depending on the organism being cultured. If provided, it can be prepared as follows: Vitamin $K_1$ Stock Solution (to be added to media): Dissolve 0.15 ml of Vitamin $K_1$ in 30 ml of 95% ethanol. Do not sterilize since it is added to media before autoclaving. Add 0.02 ml of stock solution/100 ml of medium after the medium is boiled but before it is dispensed and autoclaved. Final concentration in medium = 1 nl/ml (final concentration is about 1.0 µg/ml). Keep the Vitamin $K_1$ stock solution under refrigeration and in the dark. Discard the stock solution after about one month.

Hemin is a necessary component for the cultivation of Streptococus pneumoniae and may be required by other organisms, especially in a medium containing no blood products. Since hemin is a purified, low molecular weight product, absence of contaminating agents can be assured. It may be prepared as follows: Dissolve 50 mg hemin in 1 ml 1N NaOH; bring to 100 ml with distilled water. Autoclave at 121° C. for 15 min. Add 1 ml of this solution to 100 ml of medium.

Sodium bicarbonate is provided as a stimulating agent for growth of fastidious organisms.

L-Cysteine may or may not be required, depending on the organism cultured. If a well reduced medium for anaerobic culture is desired, addition of L-Cysteine will assist in maintainance of the reduced environment.

Glucose is provided as a carbon source, and may be replenished upon depletion. Alternate carbon sources, such as glycerol, may also be used to advantage.

HEPES buffer is added to maintain pH control. Other buffers, such as Tris, may also be used, depending on the preferred pH of culture. 0.2M HEPES at a pH of about 7.7 has been found acceptable for culture of Streptococcus pneumoniae.

The foregoing description provides a basis for modifying the specific medium formulation of this invention, while maintaining the key feature of being free of blood or bovine/ovine derived products. The method of using the medium of this invention comprises the steps of (a) preparing a stock culture on a SYG agar plate;

(b) selecting a single colony for expansion in a culture of SYG medium, and optionally preparing a frozen stock of the culture;

(c) growth of the culture in SYG, at 37° C., for about 5-24 hours, with the length of cultivation varying according to the cultured species.

SYG agar is SYG medium with 20 g/L agar. Glycerol or other cryopreservatives known in the art can be added to cultures to maintain viability of frozen stocks. Preferably, glycerol is added to a final concentration between about 15 and 25%, and preferably 17%.

The following Examples, demonstrate production and use of the medium of this invention to support the inoculum development and growth of Streptococcus pneumoniae of various serotypes, and the production by those cultures of polysaccharide. The polysaccharide thus produced is useful for the preparation of conjugate vaccines, such as those described in U.S. Pat. No. 4,695,624, herein incorporated by reference. Methods for quantitating pneumococcal polysaccharide, including immunodiffusion and radioimmunoassay are well known in the art (see for example Heidelberger, J. Exp. Med., 55, p 555 (1932); Ouchterlony, Handbook of Immunodiffusion and Immunoelectrophoresis, Ann Arbor Publishers (1968); EP 0 497 525 A2).

EXAMPLE 1

Growth of S. pneumoniae 9V

This example demonstrates development of a medium devoid of bovine or ovine derived products which supports good growth of Streptococcus pneumoniae strain 9V. Previous work resulted in growth of S. pneumoniae 9V in the commercially available PYG medium. For this example, soy peptone was used in place of animal peptone and trypticase to make modified PYG medium, which was otherwise identical to PYG medium. One lot of this medium, referred to as W001, was prepared using Sheffield HySoy peptone. A second lot, referred to as W002, was prepared using Deltown SE50M soy peptone. S. pneumoniae 9V from identical frozen stocks was inoculated into both formulations. Culture tubes were incubated at 37° C. for 14 hours. Both formulations supported growth of S. pneumoniae 9V. However, the Sheffield HySoy formulation supported much heavier growth than did the Deltown SE50M formulation. Further details of this work are presented below:

Modified PYG (W001)—HySoy—100 µL inoculum from a frozen vial.

Modified PYG (W002)—Deltown—100 µL inoculum from a frozen vial.

Liquid Mod. PYG-HySoy
  0—No growth
  100 µl—Heavy Growth, Turbid, Uniform, no sediment Liquid Mod. PYG-Deltown
  0—No growth
  100 µl—very light growth 1/10 of Hy-Soy To expand upon these observations the cultures grown in liquid broth were inoculated into #W001 and #W002 for sub-culture and determination of the best liquid formulation:

| | #W001 (hySoy) Inoculated | | | | #W002 (Deltown) Inoculated | | |
|---|---|---|---|---|---|---|---|
| 10μl | 100μl | 10μl into | 100μl | 10μl | 100μl | 10μl into | 100μl |

| Tube # | Media | 9V inco. 10 μl | 0.2M HEPES | vol 1M HEPES | phenol | phenol μl tube | pH pre inoc. | pH final | A600 pre inoc. | A600 final | visual observation |
|---|---|---|---|---|---|---|---|---|---|---|---|
| 1 | PYG | − | − | − | − | − | 6.7 | | .059 | | |
| 2 | PYG | − | − | − | + | 56 | 6.7 | | .059 | | |
| 3 | PYG | − | + | .95 ml | − | − | 7.52 | | .068 | | |
| 4 | PYG | − | + | .95 ml | + | 66 | 7.52 | | .068 | | |
| 11 | PYG | + | − | − | + | 56 | 6.7 | 6.7 | .060 | .060 | no visible growth |
| 5 | PYG | + | + | .95 ml | + | 66 | 7.52 | 6.63 | .068 | 4.31 | heavy growth, not as dense as #10 |
| 6 | SYG | − | − | − | − | − | 6.6 | | .128 | | |
| 7 | SYG | − | − | − | + | 56 | 6.6 | | .128 | | |
| 8 | SYG | − | + | .92 ml | − | − | 7.46 | | .120 | | |
| 9 | SYG | − | + | .92 ml | + | 66 | 7.46 | | .120 | | |
| 12 | SYG | + | − | − | + | 56 | 6.7 | 5.05 | .128 | 0.95 | light-fair growth |
| 10 | SYG | + | + | .92 ml | + | 66 | 7.46 | 5.38 | .120 | 6.03 | very dense growth some sediment |

| Inoculum Source | #W001 #W001 MEDIUM #W001 | #W002 #W002 #W002 | #W001 #W001 #W002 #W002 Result |
|---|---|---|---|
| HySoy liquid 10 μl | + | | good growth |
| HySoy liquid 100 μl | + | | good growth |
| HySoy liquid 10 μl | | + | very faint turbidity |
| HySoy liquid 100 μl | | + | very faint turbidity |
| Deltown liquid 10 μ | + | | good growth |
| Deltown liquid 100 μl | + | | good growth |
| Deltown liquid 10 μl | | + | faint growth |
| Deltown liquid 100 μl | | + | light growth |

Conclusions/Results

1. Liquid to liquid transfer was successful for 9V growth.
2. In all cases, media prepared with Hy-Soy provides more luxuriant, more turbid growth than the media with the Deltown SE50 m soy peptone.

The pH of the #W001 media is about 6.7 and #W002 is about 6.65. It is likely that a higher pH (about 7.5) with buffering, e.g. HEPES at 0.1M or 0.2M would support even better growth than the media without buffering.

EXAMPLE 2

Production of *S. pneumoniae* 9V Extracellular polysaccharide

The medium "SYG" supports excellent growth of *Streptococcus pneumoniae* 9V. The "SYG" uses Sheffield Hy-Soy peptone in place of peptone and trypticase, and contains 0.2M HEPES.

In this example, 9V was cultured in PYG as a positive control, with and without HEPES, pH about 7.5 and SYG with and without HEPES pH about 7.5 and the culture broth was assayed for production of *S. pneumoniae* 9V polysaccharide (Pn9VPs) using immunodiffusion and rate nephelometry.

Materials: *S. pneumoniae* 9V glycerol seed stock; 1M HEPES buffer pH 7.70 sterile filtered; PYG, Scott 3100-4807, #R7320, (about 4.75 ml/tube); SYG (mod. PYG); #W001 (~4.6 ml/tube); Phenol; Columbia Blood Agar Plates (CBA).

Method

10 μl of *S. pneumoniae* 9V inoculum was added to tubes 5, 10, 11 and 12, mixed well and incubated in a GasPak jar with $CO_2$, at 37° for 10 hrs.

The tubes were examined for growth, and the pH, A600 were measured. Phenol was added to each tube, mixed well and transferred to clean 50 ml sterile Oak Ridge tubes. The tubes were set to shake at 200 rpm. at 37° C. for 2 hrs.

After 2 hrs kill with phenol, (Note: post phenol kill-200 μl from 1:100 phenol killed broth was pipetted onto the surface of 2 CBA plates per sample. The plates were incubated at 37° C. under $CO_2$ overnight. No growth on CBA plates indicated complete killing by phenol). The tubes were centrifuged in an SS-34 rotor at 10,000 rpm, 4° C. for 20 minutes. The supernatant was removed into 4×2 ml Wheaton vials for each sample. The vials were stored at 4° C. Sample numbers 1-4 and 6-9 were mixed with the appropriate amounts of HEPES and/or phenol, mixed well and aliquotted into 4×2 ml Wheaton vials.

The CBA plates from phenol killed broth, samples #5, and #10 showed no growth. A 1 ml aliquot of 4° C. stored supernatant from samples #1, 2, 3, 4, 5, 6, 7, 8, 9, 10 was assayed for Pn 9V Ps by immunoldiffusion.

Pn 9V standard: 1.0 mg/ml and diluted to 0.5, 0.25, 0.125, 0.0625, 0.031, 0.0155 mg/ml. Intense precipitin bands were observed at each well.

Sample numbers 1, 2, 3, and 4 were media controls. No reactivity with Pn 9V antibody was seen. Sample number 5 was loaded undiluted (st), and at 1:2, 1:4, 1:8, 1:16, 1:32, 1:64 dilutions. Weak bands were seen at the undilute and 1:2 positions. The concentration of sample #5 corresponds to a band intensity of ~0.05 mg/ml compared with 9V standard.

Sample numbers 6, 7, 8 and 9 were media controls. No reactivity with 9V antibody was seen.

Sample 10 is 9V grown in SYG plus HEPES. A strong band in samples diluted to 1:8 corresponds to a polysaccharide concentration of ~0.25 mg/ml compared to 9V standard.

Sample No. 12 gave an immunodiffusion response corresponding to about 0.05 mg/ml.

All samples tested by immunodiffusion were phenol killed supernatants. stored at 4° C.

The same panel of samples was also analyzed by a Pn 9V Ps rate nephlometry assay.

Conclusions

1. All media controls were non reactive.
2. Samples 5, 10, and 12, both liquid and frozen, respond positively in the assay.
3. Samples No. 5, 10 and 12 have very different rates of response in a rate nephelometry assay. There may be several reasons for this:
   a. The 9V standard is a purified and sized 9V Ps, while the PnPs in the broth is crude, not purified or sized.
   b. The organisms may be making different sized Ps depending upon pH, A600, growth rate, time in stationary phase, etc. Therefore, Pn 9V Ps quantitation is not possible yet due to the above factors.

Results

| Tube No. | Immunodiffusion Results | Rate Nephlometry Results |
| --- | --- | --- |
| 1 | No reaction with Ab | No reaction |
| 2 | No reaction with Ab | No reaction |
| 3 | No reaction with Ab | No reaction |
| 4 | No reaction with Ab | No reaction |
| 11 | Not submitted | Not submitted |
| 5 | pos. ~0.05 mg/ml | positive liquid & −70° C. samples |
| 6 | No reaction with Ab | No reaction |
| 7 | No reaction with Ab | No reaction |
| 8 | No reaction with Ab | No reaction |
| 9 | No reaction with Ab | No reaction |
| 12 | pos. ~0.05 mg/ml | positive liquid & −70° C. samples |
| 10 | pos. ~0.05 mg/ml | positive liquid & −70° C. samples |

EXAMPLE 3

Preparation of S. pneumoniae clonally isolated master cultures

We have prepared lab stocks in SYG of S. pneumoniae 4, 6B, 9V, 14, 18C, 19F and 23F serotypes for routine lab use. They were prepared as described below.

Preparation of master lab working stock

Lyophilized cultures of S. pneumoniae were resuspended in beef heart infusion broth, inoculated into SYG liquid, and grown 6–12 hrs. Glycerol was added, and the culture was aliquoted and frozen. We made ~5 vials of each serotype. These vials are designated to be master lab working stocks. These cultures were subsequently expanded in SYG broth to make ~60 vials for each serotype.

Expansion and Preparation of Mock Premaster Cultures

A vial of S. pneumoniae frozen master lab working stock was thawed and inoculated into SYG broth and grown 6–12 hrs. Glycerol was added and the cultures aliquoted and frozen to give 60 vials for each serotype. These cultures have served as our routine lab culture source. To prepare clonally isolated pre-master cultures, a lyophilized vial of S. pneumoniae is resuspended in SYG and streaked onto SYG agar. After incubation for 12–26 hours at 37° C. under $CO_2$ a single colony was picked and streaked onto SYG agar. Plates were incubated 12–26 hours at 37° C. under $CO_2$ and a single colony was picked and inoculated into SYG liquid, and grown 6–12 hrs. Glycerol was added and the culture was aliquotted and frozen.

EXAMPLE 4

Growth of S. pneumoniae 9V and polysaccharide production in a fermentor

We have used our premaster culture of Pn 9V to inoculate 350 ml of SYG liquid. This was used to inoculate 15-L of S. pneumoniae production medium. Culture growth and polysaccharide production was equivalent to that seen when S. pneumoniae 9V was derived from blood derived cultures.

EXAMPLE 5

Growth of S. pneumoniae of other subtypes

Culture of any of the Streptococcus pneumoniae strains (Danish nomenclature based on serotype) 1, 2, 3, 4, 5, 6B, 7F, 8, 9V, 9N, 10A, 11A, 12F, 14, 15B, 17F, 18C, 19F, 19A, 20, 22F, 23F and 33F in SYG medium and inoculum development is conducted essentially as described above for S. pneumoniae 9V. Each of Streptococcus pneumoniae 4, 6B, 14, 18C, 19F, and 23F were grown in SYG and positive immunodiffusion and RIA data for pneumococcal polysaccharide production was obtained. Each serptype was grown in SYG at 37° C. under $CO_2$ for 8–24 hours. Samples were taken during growth, cells were inactivated with phenol, and supernatants were assayed for extracellular polysaccharide by immunodiffusion and quantitated by RIA:

| Serotype | Hours Growth | Start $A_{600}$ | End $A_{600}$ | Immuno-diff. | RIA µg/mL |
| --- | --- | --- | --- | --- | --- |
| 4 | 24 | 0.086 | 1.68 | + | 140 |
| 6B | 24 | 0.086 | 2.21 | + | 370 |
| 9V | 24 | 0.086 | 1.76 | + | 121 |
| 14 | 24 | 0.086 | 3.69 | + | 68 |
| 18C | 8 | 0.086 | 3.98 | + | 240 |
| 19F | 8 | 0.086 | 3.96 | + | 161 |
| 23F | 12 | 0.086 | 2.71 | + | 317 |

Based on these results, it is expected that all pneumococcal serotypes will grow adequately in the SYG medium or a modification thereof, according to this invention, and that inoculum development of pneumococcal serotypes in this medium is practical.

What is claimed is:

1. A method for clonal growth of Streptococcus pneumoniae from the single colony stage in a medium containing no bovine derived, ovine derived or crude blood derived products which comprises:

(a) preparing an agar plate of said medium streaked with said Streptococcus pneumoniae, and growing said Streptococcus pneumoniae, wherein said agar plate comprises agar, Yeast Extract, Soy Peptone, salts to maintain buffering and osmolarity, Vitamin K if known to be required for the particular strain being isolated, Hemin, Sodium Bicarbonate, L-cysteine HCl, Glucose, a buffer to maintain the pH at between about pH 7.3–7.8, but no bovine derived, ovine derived or crude blood-derived products; and (b) selecting a single colony for expansion by growing in a culture of the same medium used in step (a) absent the agar, and optionally storing the culture as a frozen glycerol stock.

2. The method of claim 1 wherein the medium in step (a) is an SYG agar plate streaked with said Streptococcus

*pneumoniae*, wherein the SYG agar plate contains, on a per liter basis, about 20 g of agar and:

| | |
|---|---|
| Yeast Extract | 10 g |
| Soy Peptone | 10 g |
| Salt Solution | 20 mL |
| Resazurin | 1 mg |
| Vitamin K | 0.5 mg |

-continued

| | |
|---|---|
| Hemin | 5 mg |
| Sodium Bicarbonate | 0.4 g |
| L-cysteine HCl | 0.85 g |
| Glucose | 10 g | wherein said salt solution contains $CaCl_2$ (0.2 g anhydrous), $MgSO4$ (0.2 g anhydrous), $K_2HPO_4$ (1.0 g), $KH_2PO_4$ (1.0 g), $NaHCO_3$ (10 g), $NaCl$ (2 g).

* * * * *